United States Patent [19]

Kato et al.

[11] 4,004,977
[45] Jan. 25, 1977

[54] METHOD FOR PURIFYING *PULLULAN*

[75] Inventors: Koso Kato; Tatsuo Nomura, both of Okayama, Japan

[73] Assignee: Kabushiki Kaisha Hayashibara Seibutsukagaku Kenkyujo, Okayama, Japan

[22] Filed: Jan. 22, 1975

[21] Appl. No.: 543,071

[30] Foreign Application Priority Data

Jan. 31, 1974 Japan .............................. 49-12263

[52] U.S. Cl. .............................. 195/31 P; 127/34; 536/1
[51] Int. Cl.$^2$ ......................................... C12D 13/04
[58] Field of Search ................. 195/31 P, 31 R, 81; 127/29, 34; 260/209 R

[56] References Cited

UNITED STATES PATENTS

| 3,436,311 | 4/1969 | Ferguson et al. | 195/31 P |
| 3,827,937 | 8/1974 | Kato et al. | 195/31 P |
| 3,870,537 | 3/1975 | Hijiya et al. | 195/31 P |
| 3,915,800 | 10/1975 | Kang et al. | 195/31 P |

OTHER PUBLICATIONS

Taguchi et al., "Structural Uniformity of Pullulan Produced by Several Strains of Pullularia pullulans", Agr. Biol. Chem. 37(7), pp. 1583–1588 (1973).
Elinov et al., "Extracellular Glucan Produced by Aureobasdium Pullulans", Chem. Abstracts, vol. 77, p. 253, No. 31328g (1972).
Neshataeva et al., "Formation of an Extra Cellular Polysaccharide by Pullularia Pullans under Semi-submerged Conditions", Chem. Abstracts, vol. 70, p. 86, No. 85130k, (1969).

*Primary Examiner*—A. Louis Monacell
*Assistant Examiner*—Thomas G. Wiseman
*Attorney, Agent, or Firm*—Browdy and Neimark

[57] ABSTRACT

A method for purifying pullulan which comprises cultivating a strain of *Aureobasidium pullulans* in a liquid medium, removing the cells from the culture broth, precipitating *pullulan* present in said broth with at least one solvent selected from the group consisting of alcohols, esters and ethers respectively with three or more carbon atoms and ketones with four or more carbon atoms to recover, and then dehydrating and/or drying the recovered *pullulan*.

3 Claims, No Drawings

METHOD FOR PURIFYING PULLULAN

Various processes are known for obtaining polysaccharide comprising liquid cultivation of a microorganism to allow extracellular elaboration of the polysaccharide, isolation and recovery of the elaborated polysaccharide. In the known processes, the culture broth is freed of cells, and to the resultant solution are added freely water-soluble organic solvents, such as low-molecular alcohols or acetone, up to a sufficient concentration for complete precipitation of the polysaccharide, and then isolation and recovery of the resultant precipitate are effected.

These prior art processes require an enormous addition of organic solvent (hereinafter referred to as solvent), usually more than a two- to three-fold volume based on the culture broth. Further, washing with absolute solvent twice or three times is necessary to effect complete dehydration. Thus, the resulting mixture will be over three to four folds in volume of the original culture broth. Accordingly, the prior art processes have a disadvantage that they will necessitate larger facilities and prolongation of the purification period. In addition, the amount ratio of required solvent to polysaccharide product will be several tens to one. Even though the solvent is recoverable by means such as distillation, the prior art processes still have another disadvantage in that the solvent will predominate a major portion in production costs. A further disadvantage of the prior art processes is the necessity of repeating further purification, dissolution and precipitation to remove the impurities i.e. residual sugars such as mono- and oligo-saccharides, pigments, protein and inorganic salts which originate from the culture broth and are present in the precipitate.

Studies and evaluations by the present inventors from various angles on processes for separation and purification of pullulan, a water-soluble polysaccharide, led to their discovery that solvents of relatively higher molecular weight and slightly lower hydrophilicity are more suitable for such processes in comparison with lower molecular and higher hydrophilic solvents used in prior art, for examples methanol, ethanol and acetone.

An advantage of the present invention is that precipitation of the polysaccharide present in culture broth is possible with a relatively smaller amount of solvent.

Another advantage of the present invention is that the employment of a solvent according to the present invention effects less precipitation of impurities which are present in the culture broth and therefore provides purer polysaccharide products.

A further advantage of the invention is that since the employment of a partially water-soluble solvent will effect formation of two to three layers, i.e. a precipitation layer of polysaccharide, a liquid layer in which water is its predominant composition (water layer) and a liquid layer primarily consisting of solvent (solvent layer) from the culture broth-solvent system, the impurities present in polysaccharide will elute in the water- and solvent-layers, which provides a more reasonable purification process than prior art which effects formation of two layers, i.e. a precipitation layer of polysaccharide and a homogeneous layer consisting of water and solvent.

According to the present invention, separation and purification with a smaller amount of solvent is possible. Accordingly, the present invention reduces the solvent loss and the cost of recovering the used solvent and also makes industrial production of polysaccharide with smaller dimensions of equipment possible. Further, the ease in removing the impurities which are present in the polysaccharide is a great advantage in purification of polysaccharide.

The present invention exhibits its outstanding efficacy especially in the cultivation method for producing pullulan, which is accompanied by simultaneous formation of a large amount of pigments, because purification of the culture broth to a colorless state can be carried out with ease. Thus, the present invention makes mass production of impurity-free pullulan possible.

The invention will be illustrated in detail with reference to a typical example. The culture broth obtained by cultivating a strain of *Aureobasidium pullulans* using a partial hydrolyzate of starch as carbon source and ammonium acetate as nitrogen source under aerobic conditions is a dark brown, viscous solution which contains 3–10%, w/v, of pullulan.

When freely water-soluble methanol is used, the addition of methanol in three-fold volume against the cell-free culture broth resulting from centrifugation will effect separation of the pullulan in a light brown colored form from the homogeneous methanol-water system. In this case the pigments present in the culture broth are adsorbed on and precipitate with the pullulan, rendering it difficult to purify of the pullulan. Further, even an addition of active carbon prior to the precipitation procedure can not effect complete decoloring and renders it difficult to filter due to the high viscosity of the culture broth, thus necessitating dilution to some extent. Therefore, the processes of the prior art have the disadvantage of requiring much more solvent in precipitating and separating pullulan.

On the contrary, since methyl ethyl ketone, a partially water-soluble substance, dissolves only 22.6%, w/w, in water, an addition of over 22.6%, w/w, of the solvent would saturate the culture broth and effect simultaneously complete precipitation of pullulan. In this case the increase in the volume of the solution to be treated is much less, about one-thirteenth, in comparison with the case of adding methanol. Also, as the solvent dissolves only in a minor portion of water and vice versa, they are separated into two layers. Most of the pigments and other impurities are dissolved in the resultant water layer, thus the pigments hardly precipitate with pullulan. Therefore, a white pullulan product is obtainable by separating and recovering the precipitated pullulan and then dehydrating in absolute solvent and/or drying the recovered pullulan. An aqueous solution prepared with the pullulan product is colorless. Impurities such as protein, mono- and oligo-saccharides and inorganic salts are hardly detected in the dried or aqueous pullulan.

More than half of the overall pullulan production costs is dependable on the costs required in the precipitation procedure with solvent and the solvent consumption. According to the present invention, the amounts of solvent used and solution to be treated can be reduced significantly in comparison with the amounts required in prior art. As the recovery of the used solvent can be carried out with ease, the industrial profit realizable by the practice of the present invention is significant. In particular the process according to the present invention is greatly effective in realizing a drastic reduction in the pullulan production cost.

The purification procedure according to the present invention is hardly affected by the method employed for cultivation. Preferably, strains which produce less pigments should be selected since the production of pullulan with microorganisms generally accompanies a large production of pigments.

After heat-sterilizing the culture broth obtained by submerged culture, the culture broth is diluted to a concentration suitble for subsequent purification procedure if it is excessively viscous. Then, the culture broth is subjected to filtration or centrifugal separation to remove the cells. To the filtrate or supernatant is added active carbon and they are again subjected to filtration or centrifugal separation to obtain a decolorized transparent solution. Thereafter, the solution may be concentrated to a stage suitable for subsequent solvent treatment, usually to a concentration not over 30%, w.v.

Suitable solvents employable in the precipitation are those with relatively low hydrophilicity, more particularly, alcohols with three or more carbon atoms such as propyl alcohol, isopropyl alcohol, n-butyl alcohol and sec-butyl alcohol, esters with three or more carbon atoms such as methyl acetate, ethers with three or more carbon atoms such as tetrahydrofuran, dioxane, ethylene glycol monoethyl ether, ethylene glycol monobutyl ether and diethylene glycol monomethyl ether, and ketones with four or more carbon atoms such as methyl ethyl ketone, diacetone alcohol and acetylacetone.

The solvents enumerated above effect precipitation and purification of pullulan with a small amount and with ease. Especially, methyl ethyl ketone, methyl acetate and sec-butyl alcohol have lower water-solubility, about 20 to 25%, and a portion thereof dissolves and is dissolved mutually in and with water to form two layers. A one-third to one-fourth, v/v, addition of such solvent to culture broth brings saturation of the resultant mixture and effects complete precipitation of pullulan. The efficacy is sufficiently realized with an addition of an amount of less than one-tenth against that of acetone or low molecular alcohol.

In this case, most of the residual sugars such as mono- and oligo-saccharides, pigments and other impurities elute satisfactorily in the water layer. In addition, slight amounts of the impurities which remain with water in the precipitated pullulan layer can be eluted and removed by adding again a small amount of the solvent to the layer. Thus, products with higher purities than those obtained by effecting precipitation with methanol or acetone, can be obtained.

In comparison with the conventionally used solvents such as methanol or acetone which require an equivalent to three-fold volume against culture broth to effect precipitation and have lower efficacy in removing impurities, some solvents described above which dissolve freely in water and vice versa but have relatively low hydrophilicity, for example, propyl alcohol, isopropyl alcohol, tetrahydrofuran, dioxane and ethylene glycol monobutyl ether, are capable of effecting complete precipitation of pullulan with an addition of less than half volume of that of the culture broth. Further, the solvents of the latter group display sufficient impurity-removing efficacy, although slightly less desirous than the above mentioned methyl ethyl ketone or methyl acetate.

The separation and recovery procedure of pullulan comprises admixing solvent to the aqueous pullulan solution, i.e. culture broth, with agitation, completely precipitating the pullulan, recovering the pullulan layer, and then adding once or twice more than an equivalent amount of solvent to the pullulan layer with sufficient agitation to recover an almost anhydrous pullulan product. Further, traces of impurities are removable by the procedure. Dried pullulan product can be prepared by separating the pullulan layer from any stage and drying the recovered layer by suitable drying method such as roller drying, fluidized-bed drying or spray drying.

The invention will be illustrated by reference to the following examples which are not intended to limit the scope of the invention.

EXAMPLE 1

A seed culture of *Aureobasidium pullulans* IFO 4464 was carried out by inoculating said strain on a sterilized and cooled liquid medium comprising 10%, w/v, acid-converted starch syrup with a D.E. (dextrose equivalent) of 45, 0.2%, w/v, $K_2HPO_4$, 0.2%, w/v, peptone, 0.2%, w/v, NaCl, 0.04%, w/v, $MgSO_4.7H_2O$ and 0.001%, w/v, $FeSO_4.7H_2O$, and incubating the resultant at 27° C under aerobic conditions for 26 hours. A main culture was carried out by inoculating the seed culture broth on a medium with the same composition as above mentioned and incubating the resultant under the same conditions for four days. The thus obtained light-brown viscous culture broth was subjected to centrifugal separation to remove the cells, and then decolorized by filtration after adding active carbon. The resulting filtrate had a pullulan content of 6%, w/v.

To 50 ml aliquots of the thus obtained viscous, transparent aqueous pullulan solution was added methyl ethyl ketone in the amounts of 16, 17, 20 and 26 ml. After sufficient agitation and mixing, the mixtures were allowed to stand to separate into the different layers. Each of the recovered layers was then assayed on its volume, coloring degree (the optical-density difference at 420nm–720nm), and residual sugar pullulan contents.

As a control, to 50 ml of the aqueous pullulan solution was added a three-fold volume of methanol, and then the mixture was agitated sufficiently and allowed stand to separate the pullulan precipitate and the water layer. The results were as listed in Table I. The recovery rate using either of the two solvents, i.e. methyl ethyl ketone and methanol, was nearly 100%. However, the pullulan products obtained with the solvents were very different in their purity and in the amount of solvent used. More particularly, in the case of methanol, much more solvent was required and the pigments that eluted in the water layer were much less than in the case where methyl ethyl ketone was used. The pullulan precipitate formed with methyl ethyl ketone was hardly colored on redissolution, and was more superior than that precipitated with methanol.

Table I

| Solvent | Volume of solvent addition (ml) | Volume of each layer (ml) | Sugar content (w/v %) | Coloring degree (420nm–720nm) |
|---|---|---|---|---|
| | 0 | (Culture broth) | (Pullulan 6.00) | 0.335 |

Table I-continued

| Solvent | Volume of solvent addition (ml) | Volume of each layer (ml) | | Sugar content (w/v %) | Coloring degree (420nm–720nm) |
|---|---|---|---|---|---|
| | | | | (Residual sugars 1.92) | |
| | 17 | M.E.K. | 0.5 | 0 | 0 |
| | | Water | 49.5 | 1.50 | 0.325 |
| | | Precipitate | 16.5 | 6.42 | 0.010 |
| M.E.K. | 20 | M.E.K. | 3.0 | 0 | 0 |
| | | Water | 50.0 | 1.52 | 0.323 |
| | | Precipitate | 16.0 | 6.40 | 0.012 |
| | 26 | M.E.K. | 9.5 | 0 | 0 |
| | | Water | 49.5 | 1.51 | 0.324 |
| | | Precipitate | 16.0 | 6.41 | 0.011 |
| Methanol | 150 | Water | 195.0 | 1.12 | 0.130 |
| | | Precipitate | 4.0 | 6.80 | 0.205 |

Notes:
M.E.K.= methyl ethyl ketone
The figures for each layer are those calculated for 50 ml of aqueous solutions.

The pullulan product obtained as above by effecting precipitation with methyl ethyl ketone still contained some amounts of water and residual sugars. After adding to the pullulan layer 25 ml of fresh methyl ethyl ketone with sufficient agitation, the separation of the precipitated layer was repeated twice and a pullulan product in powder form with a moisture content of 3%, w/w, was obtained. In fact, the product was not colored and the presence of residual sugars was hardly detected. To the contrary, the pullulan product obtained with methanol precipitation was prepared into a powder form with a moisture content of 3.2%, w/w, by the same procedure as above mentioned with 50 ml portions of methanol. But, the pullulan product was colored and the presence of 3%, w/w, of residual sugars was detected.

EXAMPLE 2

The culture broth described in Example 1 was centrifuged to remove cells. To be supernatant was added methyl acetate to effect precipitation and purification. More particularly, to 50 ml of a culture broth containing 6%, w/w, of pullulan was added 30 ml of methyl acetone. The formed pullulan layer was separted and added twice 10 ml portions of methyl acetate, dehydrated and then a pullulan product in powder form with a moisture content of 2.5%, w/w, was obtained. The purification procedure required less solvent i.e. methyl acetate, and was carried out more easily than the case where methanol was used. The assay results of the products obtained by both procedures on their pullulan and residual sugar contents and coloring degrees at 420nm–720nm are listed in Table II.

Table II

| Solvent | Volume of solvent addition (ml) | Pullulan and residual sugar contents in precipitated layer (w/v, %) | | Coloring degree (420nm–720nm) |
|---|---|---|---|---|
| | (Culture broth) | Pullulan | 6.00 | 0.335 |
| | | Residual sugars | 1.92 | |
| Methyl acetate | 30 | Pullulan | 6.00 | 0.01 |
| | | Residual sugars | 0.41 | |
| | +10 | Pullulan | 6.00 | 0.01 |
| | | Residual sugars | 0.10 | |
| | +10 | Pullulan | 6.00 | 0.01 |
| | | Residual sugars | 0.04 | |

Note:
The figures for precipitated layer are those calculated for 50 ml aqueous solutions.

EXAMPLE 3

A culture broth containing 7%, w/v, of pullulan was obtained by using the same medium described in Example 1 except tht $K_2HPO_4$ was increased to 0.3%, w/v. After removal of cells, 50 ml aliquots of the broth were taken and one of the solvents listed in Table III was added. The formed pullulan layers were separated and recovered, and then purified by adding twice 10 ml portions of the same solvent. The assay results of the thus obtained pullulan products are listed in Table III. As evident from the table each product was not colored and had low residual sugar content.

Table III

| Solvent | Volume of solvent addition (ml) | Yield of pullulan (w/w %) | Water content in pullulan product (w/w %) | Color | Residual sugar content in pullulan product (w/w %) |
|---|---|---|---|---|---|
| Diacetone alcohol | 25 | 99 | 5 | non | 1.0 |
| Acethylacetone | 30 | 98 | 2 | non | 1.5 |
| Tetrahydrofuran | 25 | 100 | 3 | non | 1.1 |
| Dioxane | 50 | 95 | 2 | non | 1.0 |
| Ethylene glycol monoethyl ether | 40 | 99 | 2 | non | 1.0 |
| Ethylene glycol monomethyl ether | 38 | 100 | 3 | non | 0.5 |
| Sec-butyl alcohol | 30 | 100 | 4 | non | 1.1 |

Note:
The figures for yield of pullulan are those calculated as the ratio of pullulan product to pullulan in culture broth.

We claim:
1. In a method for purifying pullulan which comprises cultivating a pullulan producing microorganism in a liquid medium, removing the cells from the culture broth, precipitating pullulan present in said broth with a solvent to recover the pullulan, and then dehydrating and/or drying the recovered pullulan, the improvement wherein said solvent is selected from the group consisting of esters, and ketones which have about 20 to 25% solubility in water.

2. A method according to claim 1 wherein said solvent is methyl acetate or methyl ethyl ketone.

3. A method in accordance with claim 1, wherein said solvent is one with which formation of three layers is effected in the precipitating step, a precipitation layer of pullulan, a liquid layer in which water is predominant and a solvent layer in which solvent is predominant.

* * * * *